(12) United States Patent
Takata et al.

(10) Patent No.: US 8,945,841 B2
(45) Date of Patent: Feb. 3, 2015

(54) METHOD OF JUDGING LYMPH NODE METASTASIS OF STOMACH CANCER

(75) Inventors: Hideki Takata, Kobe (JP); Kayo Shoji, Kobe (JP); Kazuki Nakabayashi, Kobe (JP); Yasuhiro Otomo, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/970,384

(22) Filed: Jan. 7, 2008

(65) Prior Publication Data

US 2008/0227094 A1 Sep. 18, 2008

(30) Foreign Application Priority Data

Jan. 15, 2007 (JP) ................. 2007-005390

(51) Int. Cl.
*C12Q 1/68* (2006.01)
*C12P 19/34* (2006.01)

(52) U.S. Cl.
CPC ............ *C12Q 1/6883* (2013.01); *C12Q 1/6851* (2013.01); *C12Q 2600/106* (2013.01); *C12Q 2600/112* (2013.01); *C12Q 2600/158* (2013.01)
USPC ............................ 435/6.12; 435/6.1; 435/6.11

(58) Field of Classification Search
None
See application file for complete search history.

(56) References Cited

U.S. PATENT DOCUMENTS

| | | | |
|---|---|---|---|
| 6,037,129 A | 3/2000 | Cole et al. | |
| 2005/0042138 A1 | 2/2005 | Ueda et al. | |
| 2005/0089857 A1 | 4/2005 | Tada et al. | |
| 2006/0121477 A1 | 6/2006 | Hochberg et al. | |
| 2006/0121515 A1* | 6/2006 | Otomo et al. | 435/6 |
| 2006/0188911 A1* | 8/2006 | Otomo et al. | 435/6 |
| 2007/0172857 A1 | 7/2007 | Daito et al. | |
| 2007/0178513 A1 | 8/2007 | Akai et al. | |
| 2007/0218496 A1 | 9/2007 | Kitagawa et al. | |
| 2007/0259360 A1 | 11/2007 | Nakabayashi et al. | |
| 2007/0287157 A1 | 12/2007 | Nakabayashi et al. | |

FOREIGN PATENT DOCUMENTS

| | | |
|---|---|---|
| CN | 1612932 | 5/2005 |
| EP | 1508809 A | 2/2005 |
| EP | 1669449 A | 6/2006 |
| EP | 1813682 A | 8/2007 |
| EP | 1845167 A | 10/2007 |
| EP | 1 867 735 A1 | 12/2007 |
| EP | 1867735 A | 12/2007 |
| JP | 2006158283 | 6/2006 |
| WO | 2004024957 A2 | 3/2004 |

OTHER PUBLICATIONS

Ignatiadis et al., "Different Prognostic Value of Cytokeratin-19 mRNA—Positive Circulating Tumor Cells According to Estrogen Receptor and HER2 Status in Early-Stage Breast Cancer," Journal of Clinical Oncology, Nov. 2007, vol. 25, No. 33, pp. 5194-5292.*
Cheung et al., "Natural variations in human gene expression assessed in lymphoblastoid cells," Nature Genetics, Mar. 2003, vol. 33, pp. 422-425.*
Jaspan et al., "Quantitative competitive reverse transcription polymerase chain reaction is not a useful method for quantification of CD4 and CD8 cell status during HIV infection," Journal of Negative Results in BioMedicine, vol. 2, No. 2, pp. 1-4.*
Bustin, S.A., "Absolute quantification of mRNA using real-time reverse transcription polymerase reaction assays," Journal of Molecular Endocrinology, 2000, vol. 25, pp. 169-193.*
Stranger et al., "Genome-Wide Associations of Gene Expression Variation in Humans," PLoS Genetics, Dec. 2005, vol. 1, No. 6, e78, pp. 0695-0704.*
Suo Jian et al, "K-19 mRNA RT-PCR in detecting micrometastasis in regional lymph nodes of gastric cancer", World Journal of Gastroenterology: WJG Aug. 28, 2006, vol. 12, No. 32, 28, pp. 5219-5222, XP002476199 ISSN: 1007-9327.
Noguchi S et al, "Detection of gastric cancer micrometastases in lymph nodes by amplification of keratin 19 mRNA with reverse transcriptase-polymerase chain reaction", Japanese Journal of Cancer Research: Gann Jun. 6, 1996, pp. 650-654, XP002476200 ISSN: 0910-5050.
Matsuda J-I et al, "Significance of metastasis detected by molecular techniques in sentinel nodes of patients with gastrointestinal cancer", Annals of Surgical Oncology, Raven Press, New York, US, vol. 11, No. 3 Suppl, Mar. 3, 2004, pp. 250S-254S, XP003005196 ISSN: 1068-9265.
Chinese Office Action dated May 25, 2010, corresponding to Chinese Application No. 200810000445.4.
Office Action for JP 2007-338580 dated Nov. 21, 2012.
Yasui et al., "Gastric Cancer: Genetic Diagnosis of Digestive Organ", Mebio, 19(10):57-61 (2012).

* cited by examiner

*Primary Examiner* — Young J Kim
(74) *Attorney, Agent, or Firm* — Sughrue Mion, PLLC

(57) ABSTRACT

Methods of judging the lymph node metastasis of stomach cancer, apparatuses for judging the lymph node metastasis of stomach cancer and kits used therefor are disclosed.

6 Claims, 11 Drawing Sheets

Flow for judgment of cancer metastasis by CPU 102d in personal computer 102

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
cagatcgaag gcctgaagga                                          20

<210> SEQ ID NO 2
<211> LENGTH: 19
<212> TYPE: DNA
<213> ORGANISM: Artificial
<220> FEATURE:
<223> OTHER INFORMATION: Primer

<400> SEQUENCE: 2
cttggcccct cagcgtact                                           19

<210> SEQ ID NO 3
<211> LENGTH: 20
<212> TYPE: DNA
```

```
<213> ORGANISM: Artificial
<220> FEATURE:
<223> OTHER INFORMATION: Primer

<400> SEQUENCE: 3
ccacactgtg cccatctacg                                                    20

<210> SEQ ID NO 4
<211> LENGTH: 26
<212> TYPE: DNA
<213> ORGANISM: Artificial
<220> FEATURE:
<223> OTHER INFORMATION: primer

<400> SEQUENCE: 4
aggatcttca tgaggtagtc agtcag                                             26

<210> SEQ ID NO 5
<211> LENGTH: 41
<212> TYPE: DNA
<213> ORGANISM: Artificial
<220> FEATURE:
<223> OTHER INFORMATION: primer

<400> SEQUENCE: 5
ggagttctca atggtggcac caactactac acgaccatcc a                            41

<210> SEQ ID NO 6
<211> LENGTH: 41
<212> TYPE: DNA
<213> ORGANISM: Artificial
<220> FEATURE:
<223> OTHER INFORMATION: primer

<400> SEQUENCE: 6
gtcctgcaga tcgacaacgc ctccgtctca aacttggttc g                            41

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
tggtaccaga agcagggg                                                      18

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
gttgatgtcg gcctccacg                                                     19

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
agaatcttgt cccgcagg                                                      18
```

```
<210> SEQ ID NO 10
<211> LENGTH: 17
<212> TYPE: DNA
<213> ORGANISM: Artificial
<220> FEATURE:
<223> OTHER INFORMATION: primer

<400> SEQUENCE: 10
cgtctggctg cagatga                                                    17

<210> SEQ ID NO 11
<211> LENGTH: 30
<212> TYPE: DNA
<213> ORGANISM: Artificial
<220> FEATURE:
<223> OTHER INFORMATION: Designed oligonucleotide sequence to act as a
      TaqMan probe

<400> SEQUENCE: 11
gcctacctga agaagaacca tgaggaggaa                                      30
```

METHOD OF JUDGING LYMPH NODE METASTASIS OF STOMACH CANCER

FIELD OF THE INVENTION

The present invention relates to a method and apparatus for judging the lymph node metastasis of stomach cancer and a reagent kit used therein.

BACKGROUND

In recent years, a genetic test is becoming rapidly widespread in the field of clinical diagnosis. As one example of the genetic test, there is the diagnosis of lymph node metastasis of cancer. Cancer cells leave from a primary focus and spread via blood vessels and lymphatic vessels to the whole body. In operation for cancer, the focus should be removed as accurately as possible, and thus the metastasis should be accurately detected, and the cancer should be suitably treated depending on the degree of metastasis. Accordingly, the diagnosis of lymph node metastasis of cancer cells during the operation is of very significant significance. As one of the techniques of diagnosing the lymph node metastasis of cancer, there is a method of detecting, as a target nucleic acid, a nucleic acid for a protein unexpressed or expressed in a low amount in normal cells, but expressed in a large amount in cancer cells. By development of gene analysis techniques in recent years, a target nucleic acid contained in lymph node tissue excised from the living body can be amplified and detected thereby effectively diagnosing cancer.

For examining the metastasis of cancer to specific tissue by the genetic test, studies on genetic test of cancer by an LAMP method (loop-mediated isothermal amplification method) or PCR (polymerase chain reaction) have been extensively conducted. This genetic test can be carried out by detecting a cancer marker contained in a tissue or a cell (for example, mRNA for a protein expressed specifically in a cancer cell).

A cancer marker (also referred hereinafter to simply as "marker"), cytokeratin 19 (CK19), is known to be useful as a marker for judging the lymph node metastasis of breast cancer. CK19 is a molecule recognized to show a significant difference in the expression level between a normal lymph node and a breast cancer cell that has metastasized to a lymph node.

In Asian countries such as China, Japan and Korea and in South America, there are many patients with stomach cancer. According to the statistics of cancer mortality in 2003 in Japan, stomach cancer is ranked second in males following lung cancer and second in females following colon cancer. Stomach cancer is a furtive disease, thus making early detection difficult, and develops often to metastasize to lymph nodes etc.

Conventionally, cytokeratin 20 and carcinoembryonic antigen have been used as markers for judging the lymph mode metastasis of stomach cancer. However, there are few reports on the genetic test of stomach cancer, and there has been demand for further development of a method for judging the lymph node metastasis of stomach cancer.

SUMMARY

The scope of the present invention is defined solely by the appended claims, and is not affected to any degree by the statements within this summary.

A first aspect of the present invention is a method of judging the lymph node metastasis of stomach cancer, comprising the steps of: quantifying mRNA of cytokeratin 19 in a detection sample prepared from a lymph node tissue suspected of having stomach cancer metastasis; and judging the presence or absence of lymph node metastasis of stomach cancer, on the basis of the obtained quantitative value of the mRNA.

A second aspect of the present invention is an apparatus for judging the lymph node metastasis of stomach cancer, comprising: a means for quantifying mRNA of cytokeratin 19 in a detection sample prepared from a lymph node tissue suspected of having stomach cancer metastasis; and a means for judging the presence or absence of lymph node metastasis of stomach cancer, on the basis of the obtained quantitative value of the mRNA.

A third aspect of the present invention is a reagent kit for judging the lymph node metastasis of stomach cancer, comprising: a pretreatment solution of a lymph node tissue for preparing a detection sample; a primer solution containing primers capable of detecting cytokeratin 19; and an enzyme solution containing an enzyme for carrying out a nucleic acid amplification method.

DETAILED DESCRIPTION OF THE PREFERRED EMBODIMENTS

Figure 1:
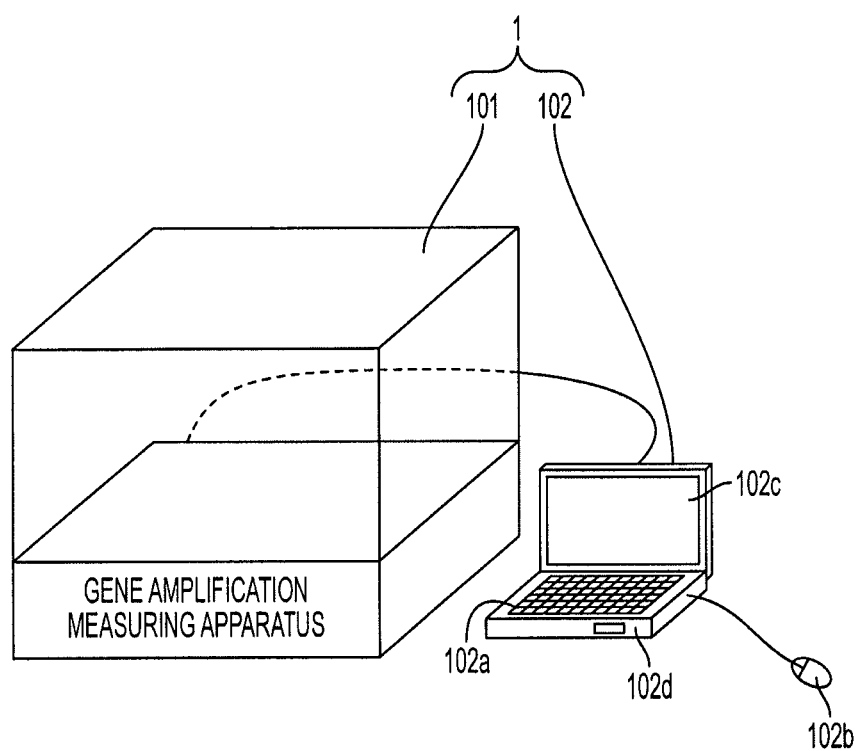
FIG. 1 is a perspective view showing the whole constitution of a judging apparatus according to an embodiment of the present invention.

In an embodiment of the present invention, the level of metastasis is not particularly limited insofar as the level of metastasis reflects the degree of metastasis or the state of a metastatic focus in a lymph node tissue to which stomach cancer has metastasized. An indicator of the level of metastasis is expressed, for example, by the size of a metastatic focus or by the number of cancer cells in a metastatic focus.

Lymph node metastasis is classified, based on size, into micrometastasis and macrometastasis. Metastasis where a metastatic focus has a major axis of less than 2 mm is referred to as micrometastasis, while metastasis where a metastatic focus has a major axis of 2 mm or more is referred to as macrometastasis. A metastatic focus of less than 0.2 mm is referred to as isolated tumor cell (ITC). Generally, it is considered necessary to excise a metastatic focus that was diagnosed as macrometastasis. Micrometastasis is regarded as a state in which whether a metastatic focus further grows or not cannot be judged. In an embodiment of the present invention, a threshold value can be established to be a value by which micrometastasis and macrometastasis can be distinguished from each other. In addition to the threshold value, a plurality of threshold values can be established according to the size of a metastatic focus.

The sample used in an embodiment of the present invention can be exemplified by a sample containing a lymph node tissue collected from a patient with stomach cancer. A more specifically, a sample includes a lymph node tissue in the vicinity of stomach cancer, collected for the purpose of biopsy.

The detection sample is not particularly limited insofar as the mRNA of cytokeratin 19 in the sample can be quantified. For example, a sample is mixed with a pretreatment solution and subjected to chemical and/or physical treatment thereby transferring (lysing) the mRNA in the cells contained in the sample into the liquid phase, thereby giving the mRNA. This solution can be used as the detection sample.

The pretreatment solution is not particularly limited insofar as it can lyse the mRNA in cells contained in a sample. The pretreatment solution includes, for example, a buffer solution etc. The buffer solution is preferably acidic to suppress RNA decomposition, and is specifically preferably in the range of pH 2.5 to 5.0, more preferably pH 3.0 to 4.0. To keep the pH in this range, known buffers can be used. Specific buffers include glycine-HCl buffer etc. The concentration of the buffer is not particularly limited insofar as the pH of the buffer solution can be kept in the above-mentioned range.

Preferably a surfactant is contained in the pretreatment solution. The cell membrane and nuclear membrane can be damaged by the surfactant, and due to this damage, a nucleic acid in a cell will move easily to the solution. Insofar as the surfactant has such action, the surfactant is not particularly limited. However, the surfactant is preferably a nonionic surfactant, more preferably a polyoxyethylene-based nonionic surfactant. The surfactant is particularly preferably a polyoxyethylene-based nonionic surfactant represented by the following formula:

$$R1\text{-}R2\text{-}(CH_2CH_2O)_n\text{-}H$$

wherein R1 represents a C10 to C22 alkyl group, alkenyl group, alkynyl group or isooctyl group; R2 represents —O— or —($C_6H_4$)—O—; and n is an integer of 8 to 120. Examples include polyoxyethylene lauryl ether, polyoxyethylene cetyl ether, polyoxyethylene oleyl ether, polyoxyethylene myristyl ether, polyoxyethylene stearyl ether, polyoxyethylene nonyl phenyl ether, and polyoxyethylene isooctyl phenyl ether. Specifically, Brij 35 (polyoxyethylene (35) lauryl ether) or the like is preferable. The concentration of the surfactant in the pretreatment solution is preferably 0.1 to 6% (v/v), more preferably 1 to 5% (v/v).

When quantification of mRNA is performed by a nucleic acid amplification method described later, dimethyl sulfoxide (DMSO) is preferably contained in the pretreatment solution. Although a substance (inhibitor) inhibiting an enzyme reaction in nucleic acid amplification may be contained in lymph nodes, the influence of this inhibitor can be effectively reduced by the action of DMSO. DMSO also has an effect of inhibiting reduction in the activity of a nucleic-acid amplification enzyme. The concentration of DMSO in the pretreatment solution is preferably 1 to 50% (v/v), more preferably 5 to 30% (v/v), most preferably 10 to 25% (v/v).

By using the pretreatment solution described above, a detection sample can be prepared easily in a short time without conducting general extraction and purification of nucleic acid with a commercial purification kit or the like.

Although the mixing ratio of the sample to the pretreatment solution is not particularly limited, about 0.0001 to 0.005 mL of the pretreatment solution can be added to and mixed with 1 mg of the sample. This mixing, though not particularly limited, can be carried out for example for such a time as to mix the sample with the pretreatment solution sufficiently at room temperature.

While the sample is mixed with the pretreatment solution, the sample in the pretreatment solution is preferably disrupted. The method of disrupting cells in the sample includes homogenization with a homogenizer and a freezing and thawing method. The homogenizer that can be used is one conventionally used in the art and includes, for example, a Waring blender, a Potter-Elvehjem homogenizer, a polytron homogenizer, a Dounce homogenizer, a French press and an ultrasonic disintegrator. Conditions for disruption are suitably established depending on the method and apparatus used.

A disruption solution of the cells prepared by the method described above can be partially purified by usual purification methods such as centrifugation, filtration and column chromatography, thereby preparing a detection sample. Depending on the state of the detection sample, the solution may be further purified by a nucleic acid extraction method.

In an embodiment of the present invention, the mRNA of cytokeratin 19 in the detection sample can be quantified by a known method using, for example, a nucleic acid amplification method, a DNA chip, etc. Particularly, a nucleic acid amplification method is preferably used.

As the DNA chip that can be used in quantification of the mRNA of cytokeratin 19, a substrate on which a polydeoxyribonucleotide capable of hybridizing with the cDNA of cytokeratin 19 and/or fragments thereof have been immobilized can be used. Detection of the RNA by the DNA chip can be carried out by a generally used method known in the art, for example in the following manner. First, a reverse transcription reaction is carried out with a primer binding to a poly A sequence present at the 3'-terminal of the mRNA in the detection sample. By using nucleotides labeled with fluorescence substances such as Cy3 and Cy5 in the reverse transcription reaction, a fluorescence-labeled cDNA is synthesized. This cDNA is then contacted with the substrate on which the polydeoxyribonucleotide has been immobilized, whereby a double strand of the polynucleotide and the labeled cDNA is formed. Then, the fluorescence of the cDNA is measured, whereby the mRNA of cytokeratin 19 can be quantified.

As the nucleic acid amplification method that can be used in quantification of the mRNA of cytokeratin 19, exemplified are nucleic acid amplification methods including a reverse transcription reaction before a nucleic acid amplification reaction, for example, known nucleic acid amplification methods such as RT-PCR (Reverse Transcription PCR) or RT-LAMP (Reverse Transcription LAMP; for LAMP, see U.S. Pat. No. 6,410,278). More specifically, a reaction solution containing the above detection sample, primers capable of detecting cytokeratin 19, and an enzyme for conducting the nucleic acid amplification method is prepared, and the resulting reaction solution can be used in nucleic acid amplification, and the cDNA thus amplified can be measured.

In an embodiment of the present invention, the primers may be provided as a primer solution. The primer solution is not particularly limited insofar as it is a solution containing primers for detecting cytokeratin 19. The primer solution is preferably a storable solution in which the primers are stable.

In an embodiment of the present invention, the enzyme for conducting the nucleic acid amplification method may be provided as an enzyme solution. The enzyme solution is not particularly limited insofar as the nucleic acid amplification method can be carried out with it. As the enzyme solution, for example, used are either enzyme solutions prepared independently from an RNA-directed DNA polymerase (reverse transcriptase) and a DNA-directed DNA polymerase (also referred hereinafter to simply as DNA polymerase) respectively or an enzyme solution containing both the reverse transcriptase and DNA polymerase. Particularly, the enzyme solution containing both the reverse transcriptase and DNA polymerase is desirable from the viewpoint of easy preparation of the reaction solution.

Conditions for the reverse transcription reaction and nucleic acid amplification reaction can vary suitably depending on primer sequence etc. Conditions that can be used in the reverse transcription reaction and nucleic acid amplification reaction are those described in, for example, Sambrook, J. et al. (1989) Molecular Cloning: A Laboratory Manual (2nd ed.), Cold Spring Harbor Laboratory Press, New York.

The primer for detecting cytokeratin 19 includes a polynucleotide capable of amplifying the mRNA of cytokeratin 19 or its cDNA. Those primers represented by the following sequences can be used, but the sequences of the primers are not particularly limited. A set of primers suitable for RT-PCR comprises primers set forth in SEQ ID NOS 1 and 2 respectively, and a set of primers suitable for RT-LAMP are set forth in SEQ ID NO 5 to 10 respectively.

```
<Primers for RT-PCR>
SEQ ID NO 1:
5'-CAGATCGAAGGCCTGAAGGA-3'

SEQ ID NO 2:
5'-CTTGGCCCCTCAGCGTACT-3'

<Primers for RT-LAMP>
SEQ ID NO 5:
5'-GGAGTTCTCAATGGTGGCACCAACTACTACACGACCATCCA-3'

SEQ ID NO 6:
5'-GTCCTGCAGATCGACAACGCCTCCGTCTCAAACTTGGTTCG-3'

SEQ ID NO 7:
5'-TGGTACCAGAAGCAGGGG-3'

SEQ ID NO 8:
5'-GTTGATGTCGGCCTCCACG-3'

SEQ ID NO 9:
5'-AGAATCTTGTCCCGCAGG-3'

SEQ ID NO 10:
5'-CGTCTGGCTGCAGATGA-3'
```

The primers mentioned above may be modified by techniques used in the art. Labeling of the primer can be conducted using a radioactive element or a nonradioactive molecule. The radioisotope used can include $^{32}P$, $^{33}P$, $^{35}P$, $^{3}H$ and $^{125}I$. The nonradioactive molecule is selected from ligands such as biotin, avidin, streptavidin and digoxigenin; haptens; dyes; and luminescent reagents such as radioluminescent, chemiluminescent, bioluminescent, fluorescent or phosphorescent reagents.

Enzymes having a reverse transcription activity, and DNA polymerase, may be those well known in the art. The enzymes having a reverse transcription activity include AMV (Avian Myeloblastosis Virus) reverse transcriptase, M-MLV (Molony Murine Leukemia Virus) reverse transcriptase, etc. The DNA polymerase that can be used includes Taq DNA polymerase, Pfu DNA polymerase, T4 DNA polymerase and Bst DNA polymerase.

By measuring the nucleic acid amplification product produced by the above nucleic acid amplification, the mRNA of cytokeratin 19 can be quantified. In this case, quantitative RT-PCR (quantitative reverse transcription-PCR) and quantitative RT-LAMP (quantitative reverse transcription-LAMP) can be preferably used. According to these methods, the optical states of the reaction solution, such as turbidity, absorbance and fluorescence intensity, are changed with amplification of the nucleic acid (cDNA) and can thus be measured in real time to quantify the mRNA of cytokeratin 19.

Specifically, methods known in the art such as the TaqMan™ method and the SYBR Green method can be used in RT-PCR. The SYBR Green method involves adding SYBR Green to a reaction solution prior to a nucleic acid amplification method and then measuring, in real time, fluorescence intensity increased with amplification of cDNA during the amplification reaction. A quantitative value of the mRNA of cytokeratin 19 can be calculated on the basis of the number of cycles required until the fluorescence intensity of the reaction solution reaches a predetermined value.

When RT-LAMP is used, a large amount of magnesium pyrophosphate is produced as a byproduct accompanying cDNA amplification. Because this magnesium pyrophosphate is insoluble, the reaction solution turns turbid as magnesium pyrophosphate is increased. Accordingly, the mRNA of cytokeratin 19 can be quantified by optically measuring, in real time, of the turbidity (or absorbance) of the reaction solution. The above-mentioned SYBR Green method can also be used in the RT-LAMP method. A quantitative value of the mRNA of cytokeratin 19 can be calculated on the basis of the time required until, for example, the turbidity, absorbance or fluorescence intensity of the reaction solution reaches a predetermined value.

In an embodiment of the present invention, a step of judging the presence or absence of lymph node metastasis of stomach cancer is not particularly limited insofar as the lymph node metastasis of stomach cancer can be absolutely or relatively judged on the basis of the quantitative value of the mRNA of cytokeratin 19 in the detection sample. It is preferable in this step that the quantitative value of the mRNA of cytokeratin 19 is compared with a threshold value.

Regardless of whether a standardization treatment is carried out or not, the quantitative value of the mRNA of cytokeratin 19 can be used in the step of judging the presence or absence of lymph node metastasis of stomach cancer. It is preferable that without conducting standardization, the absolute amount of the mRNA of cytokeratin 19 is used as the quantitative value.

With the term "standardization" as used herein, it is meant that the quantitative value obtained by quantification of the mRNA of cytokeratin 19 is converted into a value corresponding to the amount of an analyte, that is, a lymph tissue-containing sample collected from a patient with stomach cancer. More specifically, it is meant that for example, the quantitative value obtained by quantification of the mRNA of cytokeratin 19 is divided by the amount of the sample or by information reflecting said amount, preferably by the amount of an internal standard, more preferably by the amount of mRNA of a housekeeping gene or by information reflecting said amount.

The housekeeping gene is a gene generally estimated to be expressed at a constant level in many tissues and cells. The housekeeping gene includes, for example, genes for β-actin, GAPDH (glyceraldehyde-3-phosphate dehydrogenase), β2-microglobulin, and HPRT1 (hypoxanthine phosphoribosyltransferase 1). The information reflecting the amount of mRNA of a housekeeping gene refers to information obtained by quantifying the housekeeping gene in the same manner as for cytokeratin 19.

In an embodiment of the present invention, the measured value of mRNA of the housekeeping gene in a sample can be used not for standardization but as a control for judging whether nucleic acid amplification was correctly conducted. Expression of the housekeeping gene is recognized in most kinds of cells, and therefore it can be estimated that when the mRNA of the housekeeping gene is detected, the nucleic acid amplification reaction of the cancer marker was also suitably carried out. When the mRNA of the housekeeping gene is not detected, it can be estimated that the nucleic acid amplification reaction was not accurately carried out, for example due to inactivation of the enzyme.

In an embodiment of the present invention, the absolute amount of the mRNA of cytokeratin 19 refers to either the absolute amount of the mRNA of cytokeratin 19 in a detection sample subjected to mRNA quantification or information reflecting said absolute amount. When the absolute amount is to be obtained, the standardization described above is not conducted. When said absolute amount is used as quantitative value and compared directly with a previously established threshold value, the lymph node metastasis of stomach cancer can be judged more accurately than when the standardization is performed.

The conventional judgment of cancer metastasis by histological diagnosis is carried out by preparing a tissue section, subjecting it to staining and examining it under a microscope. However, it is only a part of the tissue that can be histologically examined under a microscope, so that when a section is prepared from a cancer cell-free surface, there is a possibility of overlooking cancer cells. In the judgment of cancer metastasis by molecular examination, on the other hand, the whole of an excised tissue sample (or an excessive tissue sample after preparation of a section) can be used, and thus the possibility of overlooking cancer cells is low in this molecular examination as opposed to histological examination of only a part of the section.

In an embodiment of the present invention, the threshold value can be established to be a value that is equal to, or lower than, the quantitative value of the mRNA contained in a positive sample confirmed to have the lymph node metastasis of stomach cancer and that is higher than the quantitative value of the mRNA contained in a negative sample confirmed to be free from the lymph node metastasis of stomach cancer. Quantitative values of the mRNA in a plurality of positive samples and quantitative values of the mRNA in a plurality of negative samples are previously measured, and preferably the value by which the positive samples and negative samples can be distinguished with the highest probability from each other is established as the threshold value. Specifically, the threshold value is preferably 8 to 690 copies for quantitative RT-PCR or 10 to 270 copies for quantitative RT-LAMP, in quantification of the mRNA of cytokeratin 19.

In the judgment step in the judgment method of the present invention, the presence or absence of lymph node metastasis of stomach cancer is judged on the basis of the quantitative value of the mRNA of cytokeratin 19. The quantitative value of the mRNA of cytokeratin 19 is compared with the threshold value, and when the quantitative value of the mRNA is higher than the threshold value, the tissue can be judged to be positive for lymph node metastasis, and when the quantitative value of the mRNA is lower than the threshold value, the tissue can be judged to be negative for lymph node metastasis. Such judgment result can be obtained as an indicator for determining operative procedure, excision range and postoperative therapeutic strategy.

The quantitative value of mRNA is correlated with the size of a metastatic focus or the number of cancer cells contained in a metastatic focus, depending on the level of cancer metastasis. Accordingly, the quantitative measurement or stepwise measurement of a metastatic focus in a lymph node can be carried out on the basis of the quantitative value of the mRNA as described above. In the case of stepwise measurement, the quantitative value of mRNA is compared with a plurality of previously established threshold values. In this case, at least one threshold value (first threshold value) can be established preferably so as to determine whether a sample is negative or positive for cancer. These threshold values are suitably established depending on the type of cancer or tumor marker. Even when a metastatic focus is to be quantitatively measured, it is preferable that the first threshold value is used to determine whether a sample is negative or positive for metastasis, and a sample determined to be positive for metastasis is then quantitatively measured for its cancer focus.

In an embodiment of the present invention, the first threshold value can be established so as to be a value that is equal to, or lower than, the quantitative value of the mRNA contained in a lymph node (positive sample) confirmed to contain a cancer cell and that is higher than the quantitative value of the mRNA contained in a lymph node (negative sample) confirmed to be free of a cancer cell. Quantitative values of the mRNA in a plurality of positive samples and quantitative values of the mRNA in a plurality of negative samples are previously measured, and the value by which the positive samples and negative samples can be distinguished with the highest probability from each other is preferably established as the threshold value.

When stepwise information is obtained as described above, a second threshold value is used in addition to the first threshold value. For example, the first threshold value, and a second threshold value capable of distinguishing a weak positive from a strong positive are previously established. When the quantitative value of the mRNA in a sample is lower than the first threshold value, the sample can be judged to be substantially free from a cancer focus, that is, negative for cancer. When the quantitative value of the mRNA in a sample is equal to, or higher than, the first threshold value and is simultaneously lower than the second threshold value, the sample can be judged to contain a cancer focus of relatively small size (weakly positive for cancer). When the quantitative value of the mRNA in a sample is equal to, or higher than, the second threshold value, the sample can be judged to contain a cancer focus of relatively large size (strongly positive for cancer).

Lymph node metastasis is classified based on size into micrometastasis and macrometastasis. Metastasis where a metastatic focus has a major axis of less than 2 mm is referred to as micrometastasis, while metastasis where a metastatic focus has a major axis of 2 mm or more is referred to as macrometastasis. A metastatic focus of less than 0.2 mm is referred to as an isolated tumor cell (ITC). Generally, it is considered necessary to excise a metastatic focus that was diagnosed as macrometastasis. Micrometastasis is regarded as a state in which whether a metastatic focus further grows or not cannot be judged. In an embodiment of the present invention, the second threshold value can be established to be a value by which micrometastasis and macrometastasis can be distinguished from each other. In addition to the second threshold value, a plurality of threshold values can be established according to the size of a metastatic focus.

By measuring the expression level of the mRNA of cytokeratin 19, the number of cancer cells and the size (area, volume, mass etc.) of a cancer focus, in a lymph node, can be determined. That is, the expression level of the mRNA of cytokeratin 19 in a lymph node can be an indicator for determining the area of a lymph node to be extirpated from a patient with stomach cancer. For example, when there is no large metastatic focus in the examined lymph node, the extirpation of an area larger than that is not necessary. When there is a large metastatic focus in the examined lymph node, the extirpation of an area larger than that is necessary. Theoretically, in the case of a lymph node of 4 mm or less in diameter, 2-mm macrometastasis can be accurately detected by the existing pathological diagnosis. In the case of a lymph node larger than 4 mm in diameter, there is a possibility that a metastatic focus in the lymph node is overlooked. By using the existing pathological diagnosis in combination with the method of the present invention, the possibility of overlooking a metastatic focus can be reduced.

An apparatus for judging the lymph node metastasis of stomach cancer in an embodiment of the present invention comprises a means for quantifying an mRNA of cytokeratin 19 in a detection sample prepared from a lymph node tissue collected from a patient with stomach cancer, and a means for judging the presence or absence of lymph node metastasis of stomach cancer, on the basis of the quantitative value of the mRNA.

In an embodiment of the present invention, the quantification means is not particularly limited insofar as it can quantify the mRNA of cytokeratin 19 in a detection sample prepared from a lymph node tissue collected from a patient with stomach cancer. The quantification means is preferably a nucleic acid amplification measuring apparatus that can quantify a nucleic acid amplified by LAMP or PCR. The nucleic acid amplification measuring apparatus is provided with a measuring part for measuring a nucleic acid amplification product obtained by amplifying the mRNA of cytokeratin 19 in a detection sample with primers and a nucleic acid amplification enzyme.

In an embodiment of the present invention, the judging means is not particularly limited insofar as the presence or absence of lymph node metastasis of stomach cancer can be absolutely or relatively judged on the basis of the quantitative value of the mRNA of cytokeratin 19 quantified by the quantification means described above. The judging means is preferably a means of judging cancer metastasis by comparing the quantitative value with a predetermined threshold value. The quantitative value is particularly preferably the absolute value of the mRNA of cytokeratin 19 in a detection sample. The apparatus therefor may be provided with a display for displaying the obtained judgment results.

In an embodiment of the present invention, the apparatus comprises a means for obtaining an indicator for judging the level of metastasis of a metastatic focus in a lymph node tissue. The means for obtaining an indicator may be a means other than the cancer metastasis judging means or may be integrated into one means having both the functions.

Figure 2:
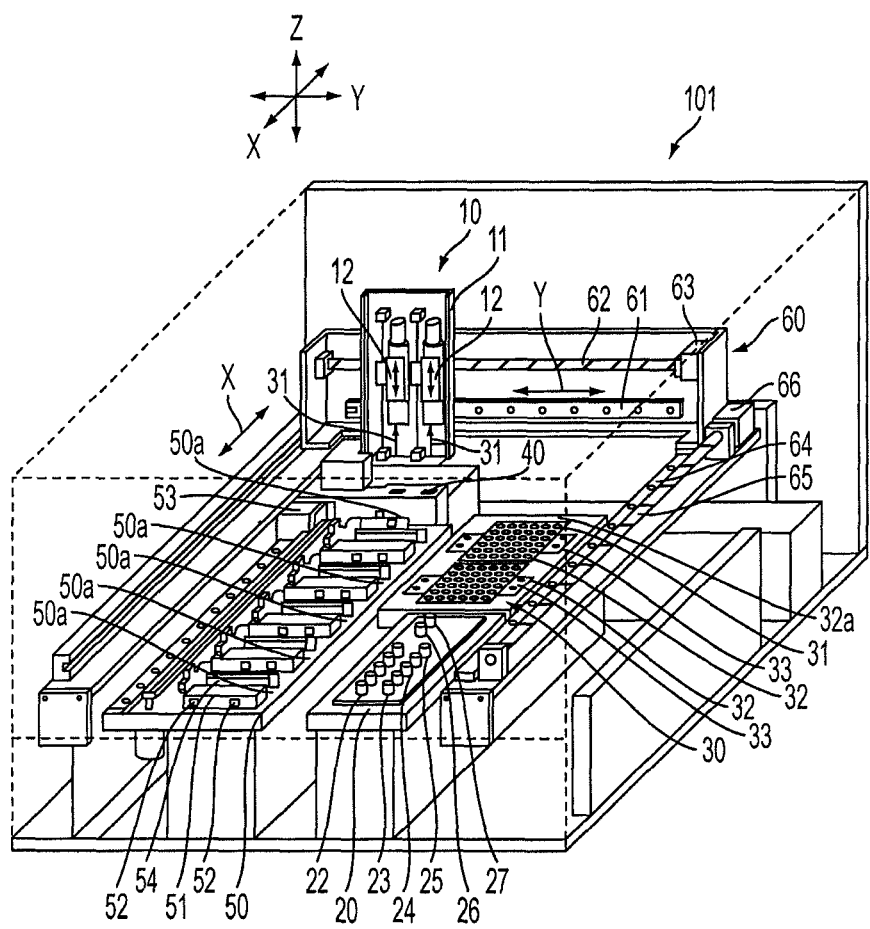
FIG. 2 is a perspective view showing the whole constitution of a nucleic acid amplification measuring apparatus as a quantification means in the judging apparatus shown in FIG. 1.
Figure 3:
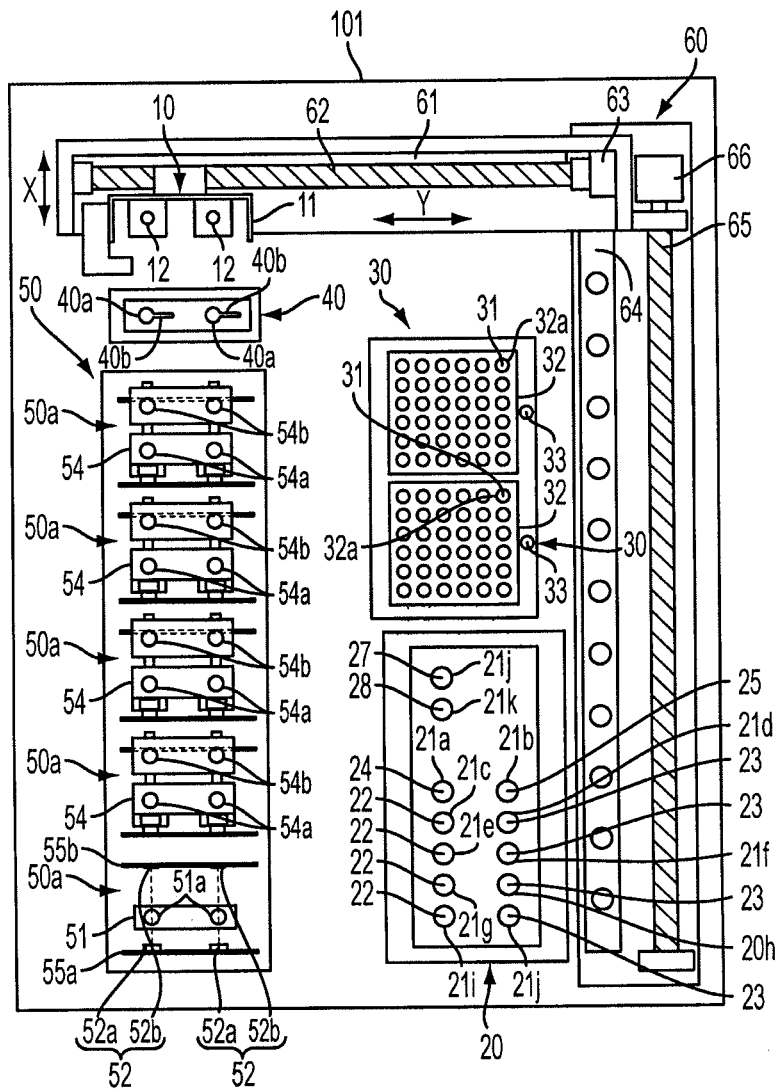
FIG. 3 is a sketchy plane view of the nucleic acid amplification measuring apparatus shown in FIG. 2.

An embodiment of the apparatus for judging the lymph node metastasis of stomach cancer is shown in FIGS. 1 to 3. FIG. 1 is a perspective view showing the whole constitution of the judging apparatus according to an embodiment of the present invention. FIG. 2 is a perspective view showing the whole constitution of a nucleic acid amplification measuring apparatus as the quantification means shown in FIG. 1. FIG. 3 is a sketchy plane view of the nucleic acid amplification measuring apparatus shown in FIG. 2.

As shown in FIG. 1, the judging apparatus in an embodiment of the present invention includes a nucleic acid amplification measuring apparatus 101 and a personal computer (PC) 102 as a judging means that is connected to, and can communicate with or without a line with, the nucleic acid amplification measuring apparatus.

As shown in FIG. 2, the nucleic acid amplification measuring apparatus 101 includes a dispensing part 10, a sample setting part 20, a chip setting part 30, a chip disposing part 40, a reaction detection part 50 composed of five reaction detection blocks 50a, and a transfer part 60 for transferring the dispensing part 10 in the X- and Y-axial directions.

As shown in FIG. 2, the dispensing part 10 includes an arm 11 being moved in the X- and Y-axial directions (horizontal direction) by the transfer part 60 and two syringes 12 that can independently move in the Z-axial direction (vertical direction) relative to the arm 11.

As shown in FIGS. 2 and 3, the sample setting part 20 is provided with ten sample container setting holes 21a to 21j, one enzyme reagent container setting hole 21k, and one primer reagent container setting hole 21l in the order from the front of the apparatus. The ten sample container setting holes 21a to 21j are arranged in 2 lines each having the 5 holes. Then, the sample container setting holes 21c and 21d, the sample container setting holes 21e and 21f, the sample container setting holes 21g and 21h, and the sample container setting holes 21i and 21j are arranged in a sample setting position 1, a sample setting position 2, a sample setting position 3 and a sample setting position 4 respectively in the order from the back of the apparatus.

In this embodiment, a sample container 22 that has contained a lysed extract (detection sample) prepared by treating (homogenizing, filtering etc.) an excised living tissue (lymph node) in advance is set in the sample container setting holes 21c, 21e, 21g and 21i in the left side of the front. A sample container 23 that has contained a diluted sample prepared by diluting the above sample 10-fold is set in the sample container setting holes 21d, 21f, 21h and 21j in the right side of the front.

A container 24 that has contained a positive control for confirming that a nucleic acid to be amplified is normally amplified is arranged in the sample container setting hole 21a. A container 25 that has contained a negative control for confirming that a nucleic acid not to be amplified is normally not amplified is arranged in the sample container setting hole 21b.

An enzyme reagent container 26 that has contained a nucleic acid amplification enzyme reagent for amplifying a cDNA corresponding to the mRNA of cytokeratin 19 (also referred to simply as CK19), and a primer reagent container 27 that has contained a primer reagent for CK19 are set in an enzyme reagent container setting hole 21k and a primer reagent container setting hole 21l, respectively.

As shown in FIGS. 2 and 3, each of the reaction detection blocks 50a in the reaction detection part 50 is composed of a reaction part 51, two turbidity detection parts 52, and a lid closing part 53 (see FIG. 2). As shown in FIG. 3, the reaction part 51 arranged in each reaction detection block 50a is provided with two detection cell setting holes 51a for setting a detection cell 54. The reaction detection blocks 50a are arranged in a cell setting position 1, a cell setting position 2, a cell setting position 3, a cell setting position 4 and a cell setting position 5 respectively in the order from the back of the apparatus.

The turbidity detecting part 52 is composed of (i) a LED light source 52a consisting of a blue LED having a wavelength of 465 nm attached to a substrate 55a arranged on one side of the reaction part 51, and (ii) a photodiode light receiving part 52b attached to a substrate 55b arranged on the other side of the reaction part 51. Each reaction detection block 50a is provided with two of turbidity detection parts 52, the turbidity detection part 52 including one LED light source 52a and one photodiode light receiving part 52b.

The detection cell 54 has two cell parts 54a for accommodating a sample and two lids 54b for closing the two cell parts 54a.

As shown in FIG. 2, a transfer part 60 includes a translatory guide 61 and a ball screw 62 for transferring the dispensing part 10 in the Y-axial direction, a stepping motor 63 for driving the ball screw 62, a translatory guide 64 and a ball screw 65 for transferring the dispensing part 10 in the X-axial direction, and a stepping motor 66 for driving the ball screw 65. The transfer of the dispensing part 10 in the X- and Y-axial directions is carried out by rotating the ball screws 62 and 65 with the stepping motors 63 and 66, respectively.

As shown in FIG. 1, the personal computer 102 includes input devices that are keyboard 102a and mouse 102b, a display 102c consisting of a monitor, and CPU 102d for analyzing the measurement result of a sample.

Now, the working of the judgement apparatus 1 in this embodiment is described by reference to FIGS. 1 to 3. In this embodiment, described is the apparatus in which (i) the mRNA of cytokeratin 19 present in a lymph node tissue excised in stomach cancer operation is amplified by LAMP, (ii) a change in turbidity attributable to the white turbidity of magnesium pyrophosphate produced accompanying amplification is measured thereby quantifying the mRNA of cytokeratin 19, and (iii) the quantitative value are compared with a threshold value as described above, whereby the presence or absence of lymph node metastasis is judged.

A sample container 22 that has contained a lysed extract prepared by treating (for example, homogenizing, filtering etc.) an excised tissue in advance is set in sample container setting holes 21c to 21j (see FIGS. 2 and 3). A container 24 that has contained a positive control and a container 25 that has contained a negative control are set in sample container setting holes 21a and 21b respectively (see FIG. 3). An enzyme reagent container 26 that has contained a nucleic acid amplification enzyme reagent for amplification of CK19 and a primer reagent container 27 that has contained a primer reagent for amplification of CK19 are set in an enzyme reagent container setting hole 21k and a primer reagent container setting hole 21l respectively (see FIG. 3). Two racks 32 that have contained thirty-six of disposable pipette chips 31 are arranged in a chip setting part 30.

When the operation of the nucleic acid amplification measuring apparatus 101 is started, an arm 11 of the dispensing part 10 is transferred from the start position to the chip setting part 30 by the transfer part 60 shown in FIG. 2, and then in the chip setting part 30, two syringes 12 of the dispensing part 10 are transferred downward. The tips of the nozzles of the two syringes 12 are pressed into the upper openings of the two pipette chips 31 and thus the pipette chips 31 are automatically fitted into the tips of the nozzles of the two syringes 12. Then, the two syringes 12 are transferred upward and then the arm 11 of the dispensing part 10 is transferred in the X-axial direction toward the upside of the primer reagent container 27 that has contained a primer reagent for CK19. Then, one of syringe 12 positioned in the upside of the primer reagent container 27 is transferred downward, to suck up the primer reagent, and then transferred upward. Thereafter, the arm 11 of the dispensing part 10 is transferred in the Y-axial direction by the transfer part 60 until the other syringe 12 is positioned in the upside of the same primer reagent container 27. Then, the other syringe 12 is transferred downward, to suck up the primer reagent from the same primer reagent container 27, and then transferred upward. In this manner, the primer reagent for CK19 in the primer reagent container 27 is sucked up by the two pipette chips 31 fitted into the syringes 12.

The two syringes 12 that have sucked up the primer reagent are transferred upward, and then the arm 11 of the dispensing part 10 is transferred by the transfer part 60 to the upside of the reaction detection block 50a positioned in the cell setting position 1 in the backmost side (backside of the front of the apparatus). In the reaction detection block 50a in the backmost side, the two syringes 12 are transferred downward, whereby the two pipette chips 31 fitted into the two syringes 12 are inserted respectively into two cell parts 54a of the detection cell 54. Using the syringes 12, the primer reagent of CK19 is discharged into the two cell parts 54a respectively. The syringes 12 discharge the primer reagent and then move upward.

After the two syringes 12 that have discharged the primer reagent, the arm 11 of the dispensing part 10 is transferred in the X-axial direction toward the upside of a chip disposing part 40 by the transfer part 60. Then, the pipette chip 31 is disposed of in the chip disposing part 40. Specifically, the two syringes 12 are transferred downward, whereby the pipette chips 31 are inserted into two chip disposing holes 40a of the chip disposing part 40 (see FIG. 3). In this state, the arm 11 of the dispensing part 10 is transferred in the Y-axial direction by the transfer part 60, thereby transferring the pipette chips 31 below groove 40b. Then, the two syringes 12 are transferred upward, whereby a collar element of the upper surface of the pipette chip 31 is abutted against the lower sides of the groove 40b and receives downward force from the lower sides, and thus the pipette chips 31 are automatically detached from the nozzles of the two syringes 12. The pipette chips 31 are thereby disposed of in the chip disposing part 40.

Then, the enzyme reagent is discharged from the enzyme reagent container 26 into the cell part 54a by the same movement, and the samples are discharged from the sample containers 22 and 23 into the cell parts 54a by the same movement.

Then, the primer reagent, the enzyme reagent and the sample are discharged into the cell part 54a, and then the lid 54b of the detection cell 54 is closed. After the lid is closed, the temperature of the liquid in the detection cell 54 is risen from about 20° C. to about 65° C., whereby a cDNA corresponding to the mRNA of CK19 is amplified by RT-LAMP reaction. Then, white turbidity attributable to magnesium pyrophosphate produced accompanying amplification is detected by turbidimetry. Specifically, turbidity is detected by detecting (monitoring) the turbidity in the detection cell 54 during amplification reaction, by using a LED light source 52a and a photodiode light receiving part 52b shown in FIG. 3.

Turbidity data of the samples are sent from the nucleic acid amplification measuring apparatus 101 to the personal computer 102 in real time. By CPU 102d in the personal computer 102, the turbidity data of the samples are compared with a predetermined threshold value, thereby judging the presence or absence of lymph node metastasis of stomach cancer. Simultaneously, the size of a metastatic focus in lymph node may be judged.

Figure 4:
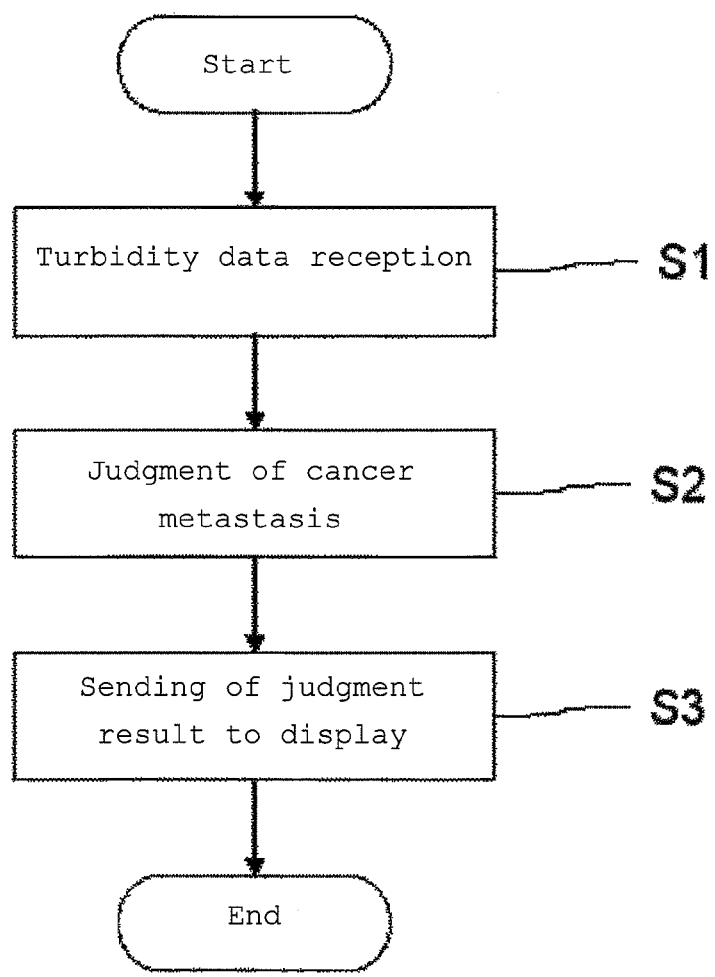
FIG. 4 is a flow for judgment of metastasis by CPU in a personal computer as a judging means in the judging apparatus according to an embodiment of the present invention.

Now, processing in CPU 102d of the personal computer 102 is described by reference to FIG. 4. In step S1, CPU 102d first receives the turbidity data of the sample from the nucleic acid amplification measuring apparatus 101. In step S2, CPU 120d then compares the turbidity data with a predetermined threshold value, thereby judging whether the lymph node metastasis of stomach cancer is positive or negative. In step S3, the result judged in the step S2 is then sent to the display 102c.

EXAMPLES

In these examples, described are the method of judging the lymph node metastasis of stomach cancer by quantifying the mRNA of CK19 in a lymph node tissue collected from a patient with stomach cancer.

Example 1

Judgment of Lymph Node Metastasis of Stomach Cancer by Quantitative RT-PCR (1) Preparation of a Detection Sample Ten lymph nodes (positive lymph nodes) histologically recognized to undergo stomach cancer metastasis and 10 lymph nodes (negative lymph nodes) histologically not recognized to undergo stomach cancer metastasis were used to prepare detection samples in the following manner.

First, 4 mL of a DMSO-containing treatment solution, pH 3.4 (200 mM glycine-HCl, 5% Brij 35 (polyoxyethylene (35) lauryl ether, manufactured by SIGMA) and 20% DMSO (Wako Pure Chemical Industries, Ltd.)) was added to each lymph node (about 50 to 600 mg/lymph node) which was then homogenized with a blender. The resulting homogenate was centrifuged at 10,000×g at room temperature for 1 minute, and RNA was extracted and purified from 200 µl of the supernatant by an RNeasy Mini kit (Catalog No. 74014, manufactured by Qiagen) to give a detection sample.

(2) Quantification of mRNA of CK19

The detection samples obtained from the positive lymph nodes and negative lymph nodes by the method described above were subjected to real-time RT-PCR with a real-time PCR apparatus (ABI Prism™ 7000 Sequence Detection System, Applied Biosystems) with the following primers, to quantify the mRNA of CK19.

The real-time RT-PCR was carried out using an RT-PCR kit, that is, a Quanti Tect SYBR Green RT-PCR kit (Catalog No. 204245, manufactured by Qiagen) according to the manufacture's instructions. The composition of the reaction solution and the reaction conditions are as follows.

Primers for Detecting CK19:

```
                                         (SEQ ID NO: 1)
Forward primer:    5'-CAGATCGAAGGCCTGAAGGA-3'

(SEQ ID NO: 2)
Reverse primer:    5'-CTTGGCCCCTCAGCGTACT-3'
```

Reaction Solution:

| | |
|---|---|
| RNase-free H$_2$O | 11.1 µL |
| 2xMaster Mix | 12.50 µL |
| 100 µM forward primer (final concentration 500 nM) | 0.075 µL |
| 100 µM reverse primer (final concentration 500 nM) | 0.075 µL |
| Quanti Tect RT Mix | 0.25 µL |
| Detection sample | 1.00 µL |
| Total | 25.00 µL |

Figure 5:
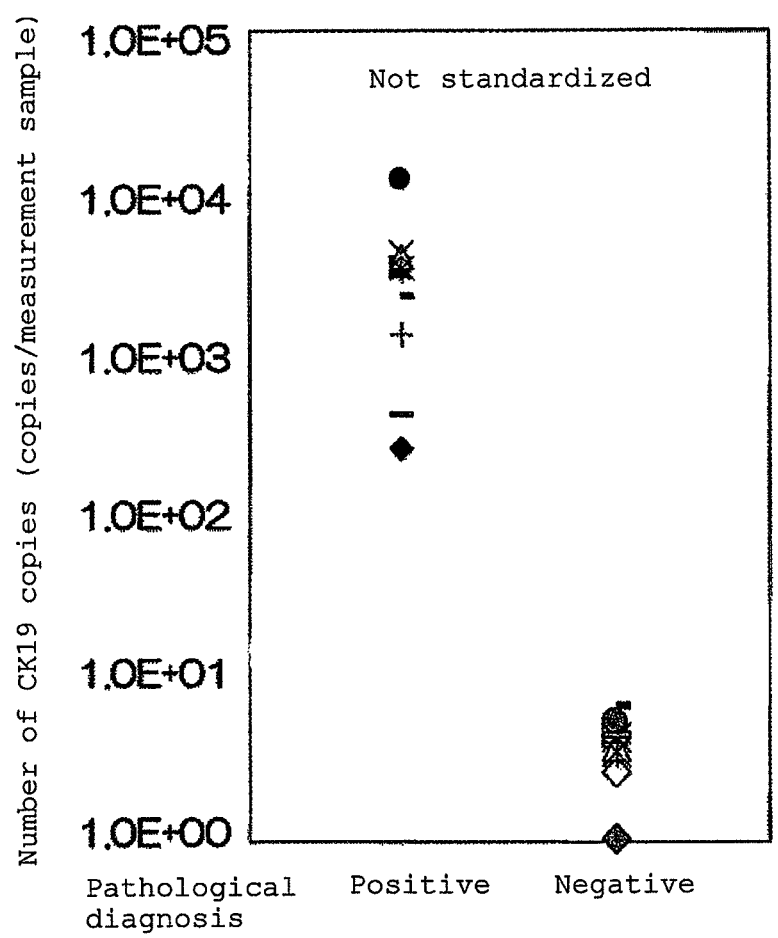
FIG. 5 is a graph showing the number of copies of mRNA of CK19 in a lymph node tissue with stomach cancer. The number was calculated in Example 1.

Reaction Conditions:
50° C., 30 minutes
95° C., 15 minutes
PCR: 40 cycles of the following steps
95° C., 15 seconds
53° C., 30 seconds
72° C., 30 seconds The number of PCR cycles by which the fluorescence intensity of the reaction solution had exceeded a standard value (threshold: a value automatically established with SDS software installed in the real-time PCR apparatus) was determined, and on the basis of this value, the number of mRNA copies was calculated. The results are shown in FIG. 5. From the results in FIG. 5, it can be seen that by establishing the threshold value to be 350 copies per detection sample, the presence or absence of metastasis of stomach cancer can be judged in accordance with the result of tissue diagnosis.

Example 2

As the housekeeping gene, the amount of mRNA of β-actin in the detection sample was measured. This measurement was carried out in the same manner as in measurement of the mRNA of CK19 in Example 1. Primers used in PCR were as follows.

Primers for Detecting β-Actin:

```
Forward primer:
5'-CCACACTGTGCCCATCTACG-3'        (SEQ ID NO: 3)

Reverse primer:
5'-AGGATCTTCATGAGGTAGTCAGTCAG-3'  (SEQ ID NO: 4)
```

Figure 6:
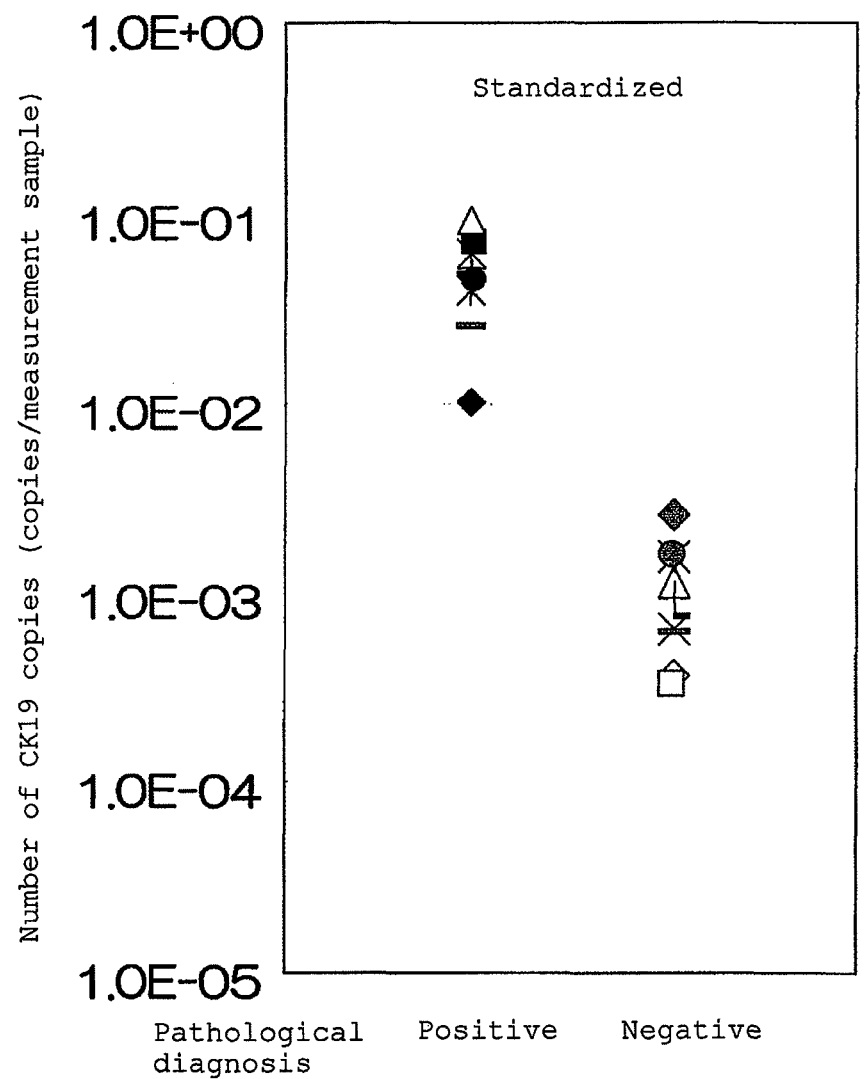
FIG. 6 is a graph showing a standardized value of mRNA of CK19 in a lymph node tissue with stomach cancer. The number was calculated in Example 2.

The number of mRNA copies of CK19 obtained in Example 1 was divided (standardized) by the number of mRNA copies of β-actin obtained in this example. The results are shown in FIG. 6. From the results in FIG. 6, it can be seen that the presence or absence of lymph node metastasis of stomach cancer can also be judged when the number of mRNA copies of CK19 was standardized by dividing it by the number of mRNA copies of β-actin as a housekeeping gene.

From the results in Examples 1 and 2, it was revealed that the presence or absence of lymph node metastasis of stomach cancer can be judged from the quantitative value of the mRNA of CK19 by quantitative RT-PCR. It was also revealed that the positive samples and negative samples can be distinguished from each other more clearly by using, as quantitative value, the absolute amount of the mRNA of CK19.

Example 3

Judgment of Lymph Node Metastasis of Stomach Cancer by Quantitative RT-LAMP (1) Preparation of a Detection Sample Seven lymph nodes (positive lymph nodes) histologically recognized to undergo stomach cancer metastasis and 8 lymph nodes (negative lymph nodes) histologically not recognized to undergo stomach cancer metastasis were used to prepare detection samples in the following manner.

First, 4 mL of a DMSO-containing treatment solution, pH 3.4 (200 mM glycine-HCl, 5% Brij 35 (polyoxyethylene (35) lauryl ether, manufactured by SIGMA) and 20% DMSO (Wako Pure Chemical Industries, Ltd.)) was added to each lymph node (about 50 to 600 mg/lymph node) which was then homogenized with a blender. The resulting homogenate was centrifuged at 10,000×g at room temperature for 1 minute, and 180 µL treatment solution was added to 20 µL of the supernatant, to prepare a detection sample (200 µL).

(2) Preparation of a Reaction Solution

The following components were mixed to prepare 13.97 µl reaction solution.

| | |
|---|---|
| 750 mM Tris buffer (pH 8.0) | 1.00 µl |
| 10x Thermopol buffer (manufactured by New England Bio Laboratory) | 2.50 µl |
| 10 mM dNTPs | 2.00 µl |
| 100 mM MgSO$_4$ | 0.75 µl |
| 100 mM dithiothreitol | 1.25 µl |
| 2% Tergitol (manufactured by Sigma Aldrich Japan) | 2.50 µl |
| H$_2$O | 3.97 µl |

(3) Preparation of an Enzyme Reagent

The following components were mixed to prepare 3.04 µl enzyme reagent.

| | |
|---|---|
| 10 U/µl AMV reverse transcriptase (Promega) | 0.14 µl |
| 8 U/µl Bst DNA polymerase (manufactured by New England Bio Laboratory) | 2.27 µl |
| RNase inhibitor (Promega) | 0.63 µl |

(4) Preparation of Primers

The following components were mixed to prepare 6.00 µl primer solution.

```
80 pmol/µl forward inner primer              1.00 µl
(SEQ ID NO 5: 5'-GGAGTTCTCAATGGTGGCACCAACTACTACACG
ACCATCCA-3')

80 pmol/µl reverse inner primer              1.00 µl
(SEQ ID NO 6: 5'-GTCCTGCAGATCGACAACGCCTCCGTCTCAAAC
TTGGTTCG-3')

5 pmol/µl forward outer primer              1.00 µl
(SEQ ID NO 7: 5'-TGGTACCAGAAGCAGGGG-3')

5 pmol/µl reverse outer primer              1.00 µl
(SEQ ID NO 8: 5'-GTTGATGTCGGCCTCCACG-3')

60 pmol/µl forward loop primer               1.00 µl
(SEQ ID NO 9: 5'-AGAATCTTGTCCCGCAGG-3')

60 pmol/µl reverse loop primer               1.00 µl
(SEQ ID NO 10: 5'-CGTCTGGCTGCAGATGA-3')
```

(5) Preparation of RT-LAMP Reaction Solution

An RT-LAMP reaction solution consisting of the reaction solution, the enzyme reagent and the primer reagent was prepared. The RT-LAMP reaction solution is a reaction solution for amplifying cDNA by RT-LAMP method with the mRNA of CK19 as a template.

(6) Quantification of mRNA of CK19

Two µl of the detection sample was added to 23 µl of RT-LAMP reaction solution, and the white turbidity of insoluble magnesium pyrophosphate as a byproduct produced simultaneously with nucleic acid amplification was measured in real time with a real-time turbidity measuring apparatus (LA-200 manufactured by Teramex).

Figure 7:
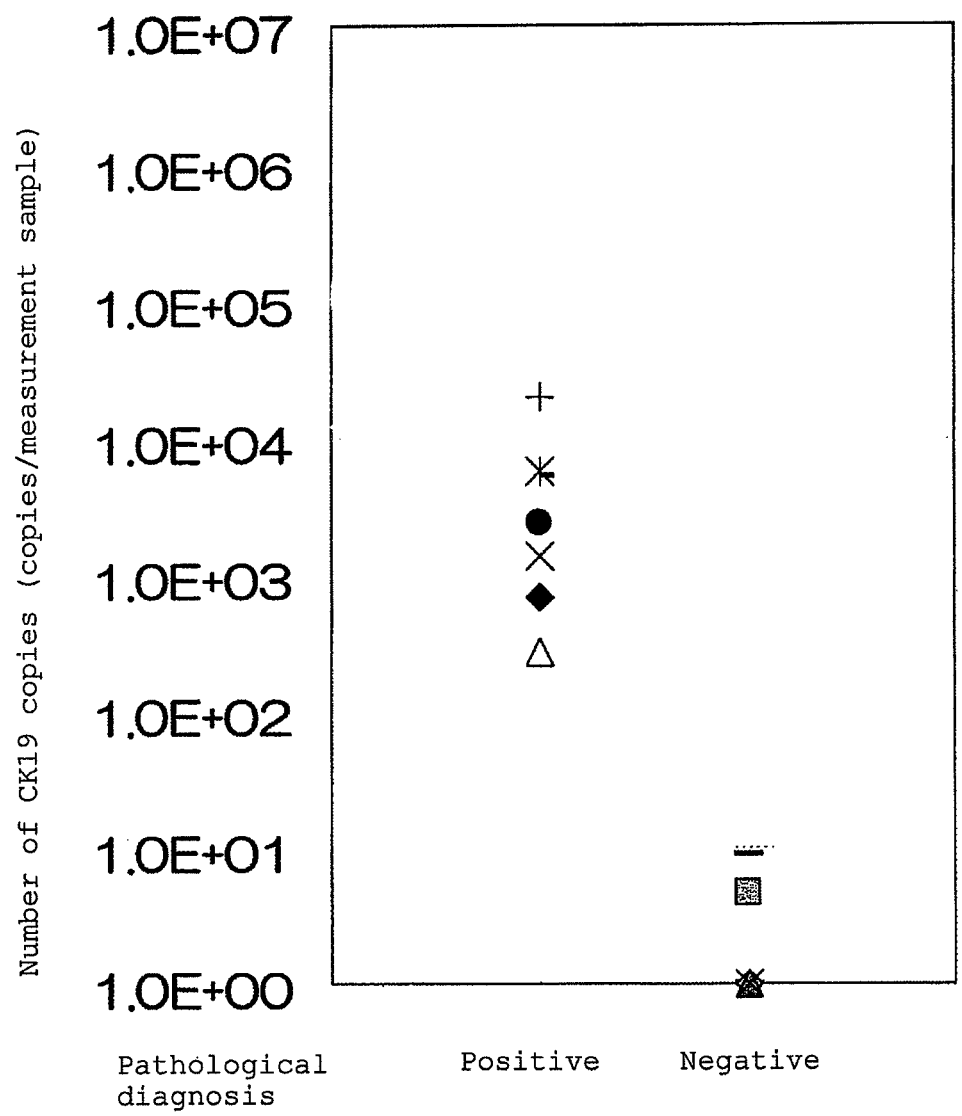
FIG. 7 is a graph showing the number of copies of mRNA of CK19 in a lymph node tissue with stomach cancer. The number was calculated in Example 3.

The time (detection time) that had elapsed until the turbidity of the reaction solution reached 0.1 by RT-LAMP amplification of cDNA corresponding to the mRNA contained in each sample was determined. On the basis of this value, the absolute amount of the mRNA of CK19 was calculated. The results are shown in FIG. 7. From the results in FIG. 7, it can be seen that by establishing the threshold value to be 140 copies per detection sample, the presence or absence of metastasis of stomach cancer can be judged in accordance with the result of tissue diagnosis.

From the results in Example 3, it was revealed that, from the quantitative value of the mRNA of CK19 determined by quantitative RT-LAMP, the presence or absence of lymph node metastasis of stomach cancer can also be judged.

From the foregoing, it was found that accurate judgment results of lymph node metastasis of stomach cancer can be obtained on the basis of the quantitative value of the mRNA of cytokeratin 19 in detection samples. It was also revealed that the method of judging the presence or absence of lymph node metastasis of stomach cancer according to the present invention can be used in effective judgment regardless of the type of the mRNA quantification method, particularly the nucleic acid amplification method.

Example 4

Judgment of the Size of a Lymph Node Metastatic Focus by Quantitative RT-PCR

Eleven lymph nodes obtained from 9 patients with stomach cancer were measured for the number of cancer cells and for the expression level of CK19 mRNA.

(1) Measurement of the Size of a Metastatic Focus and Counting of Cancer Cells

A section of 10 µm in thickness was prepared from each of 11 lymph nodes to which stomach cancer (non-solid low-differentiated adenocarcinoma) had metastasized, and the section was mounted on a glass slide. This section was subjected to immunohistochemical staining with anti-CK19 antibody and Envision Kit (both of which are available from DAKO Ltd.). The size (mm$^2$) of a metastatic focus of cancer cells in this section was measured using GS-710 Calibrated Densitomer (Bio-Rad). Using WinROOF (Mitani Corporation), the number of cancer cells (number of cells/section) was determined.

(2) Quantification of CK19 mRNA

A section (about 10 µm in thickness) adjacent to the section cut in the step (1) above was cut off and subjected to RNA extraction with RNeasy Mini Kit (Qiagen) to prepare an RNA sample. This RNA sample was used to prepare a reaction solution with the following composition, and the number of copies (copies/section) of CK19 mRNA was calculated according to the TaqMan method. The measurement according to the TaqMan method was carried out by using TaqMan One-step RT-PCR Master Mix and Prism 7000 Real-time PCR system (both of which are available from Applied Biosystems) according to the manufacture's instructions.

Reaction Solution:

| | |
|---|---|
| RNase free H$_2$O | 10.205 µL |
| TaqMan 2X Universal PCR Master Mix | 12.5 µL |
| 40X MultiScribe and RNase Inhibitor Mix | 0.63 µL |
| 100 µM forward primer | 0.075 µL |

| | |
|---|---|
| 100 µM reverse primer | 0.075 µL |
| 9.7 pmol/µL (final concentration, 200 nm) | 0.515 µL |
| TaqMan probe | |
| Detection sample | 1 µL |
| Total | 25.00 µL |

The primer sequences for detection of CK19 mRNA and the sequence of TaqMan probe are as follows:

```
Forward primer:
                                           (SEQ ID NO: 1)
5'-CAGATCGAAGGCCTGAAGGA-3'

Reverse primer:
                                           (SEQ ID NO: 2)
5'-CTTGGCCCCTCAGCGTACT-3'

TaqMan probe:
                                           (SEQ ID NO: 11)
5'-GCCTACCTGAAGAAGAACCATGAGGAGGAA-3'
```

Figure 8:
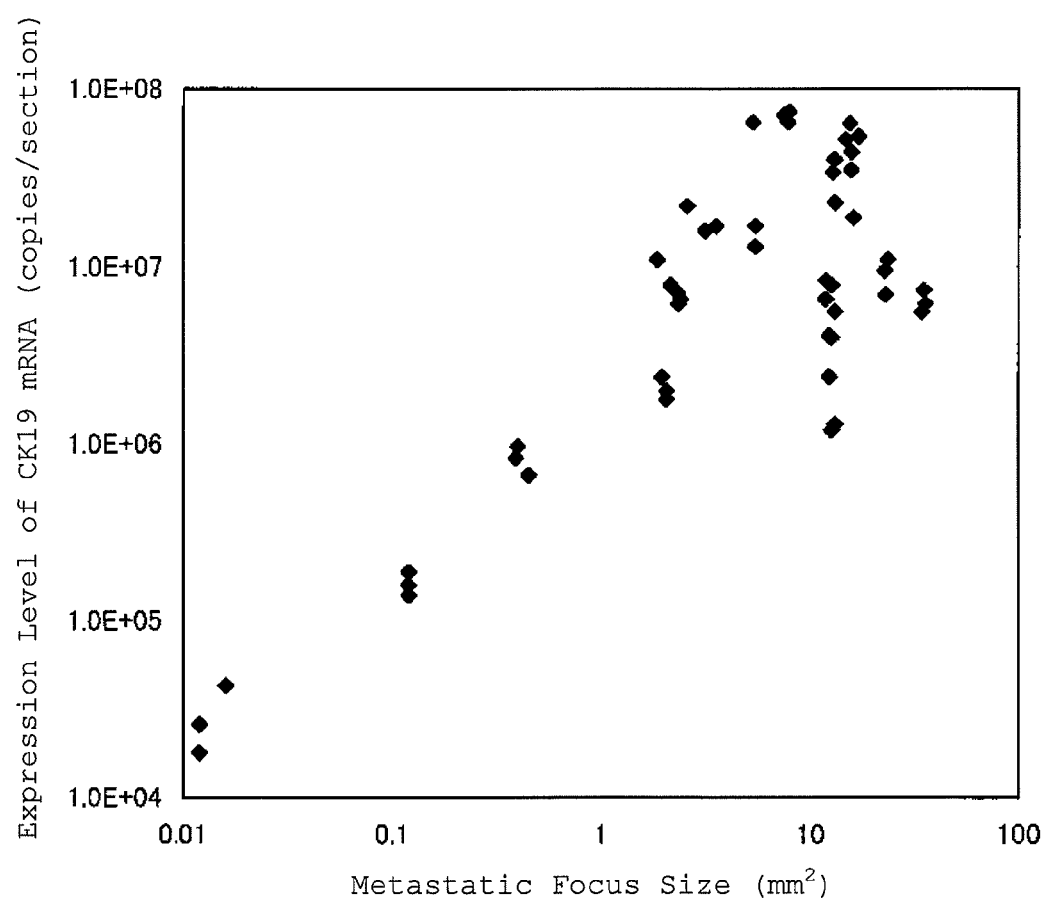
FIG. 8 is a graph showing the relationship between a quantitative value of mRNA of CK19 and the size of a metastatic focus.
Figure 9:
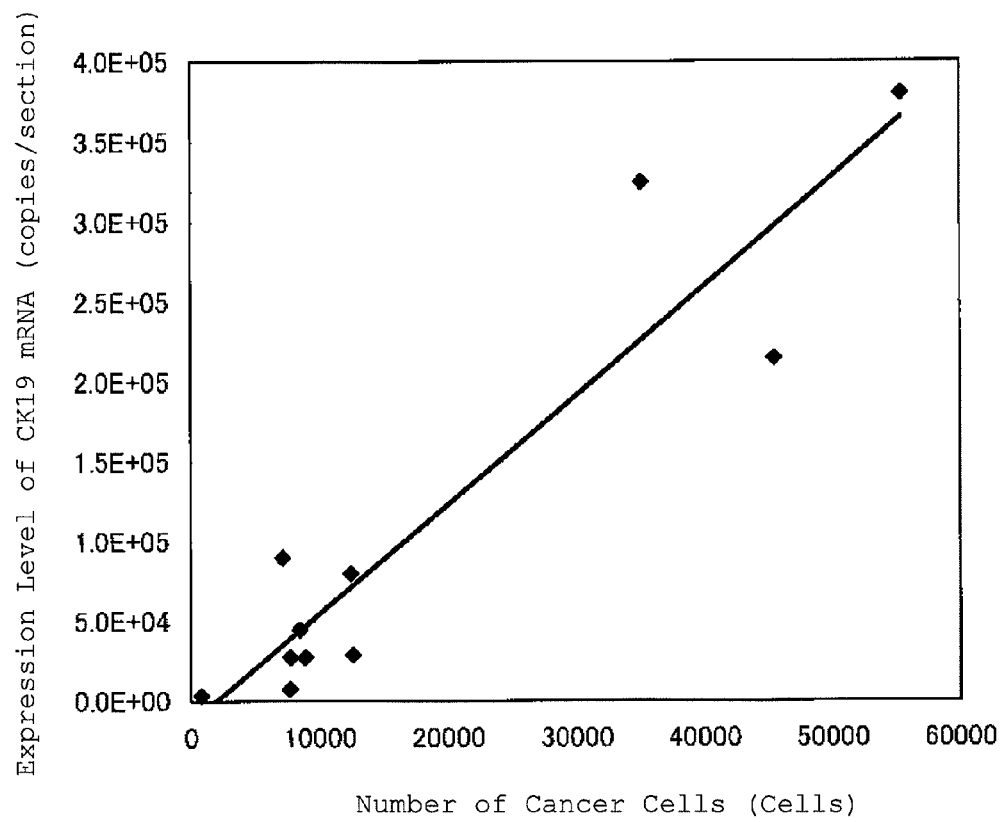
FIG. 9 is a graph showing the relationship between a quantitative value of mRNA of CK19 and the number of cancer cells.

The TaqMan probe has a 6-carboxyfluorescein (FAM) at the 5'-terminal and 6-carboxy-tetramethyl-rhodamine (TAMRA) at the 3'-terminal thereof.
Reaction Conditions:
48° C., 30 minutes
95° C., 10 minutes
PCR: 40 cycles of the following steps
95° C., 15 seconds
60° C., 1 minute The relationship between the quantitative value of mRNA (copies/section) and the size of a stomach cancer metastatic focus is shown in FIG. 8. The relationship between the quantitative value and the number of cancer cells is shown in FIG. 9. From FIGS. 8 and 9, it was recognized that the quantitative value of CK19 mRNA is correlated with the size of a metastatic focus and the number of cancer cells. Accordingly, it was confirmed that the size of the metastatic focus can be estimated by quantifying the CK19 mRNA in the lymph node.

Example 5

Measurement of the Size of a Lymph-Node Metastatic Focus by Quantitative RT-LAMP Eleven lymph nodes obtained from 9 patients with stomach cancer were measured for the number of cancer cells and for the expression level of CK19 mRNA.
(1) Measurement of the Size of a Metastatic Focus and Counting of Cancer Cells
According to the method described in the step (1) in Example 4, a section of 10 µm in thickness was prepared from each of 11 lymph nodes to which stomach cancer (non-solid low-differentiated adenocarcinoma) had metastasized, and the section was subjected to immunohistochemical staining. According to the method described in the step (1) in Example 4, the size ($mm^2$) of a metastatic focus of cancer cells in the section was then measured. According to the method described in the step (1) in Example 4, the number of cancer cells (number of cells/section) was determined.
(2) Quantification of CK19 mRNA
A section (about 10 µm in thickness) adjacent to the section cut in the step (1) above was cut off and subjected to RNA extraction with RNeasy Mini Kit (Qiagen) to prepare an RNA sample. According to the method described in Example 3, a reaction solution was prepared and subjected to RT-LAMP.

Figure 10:
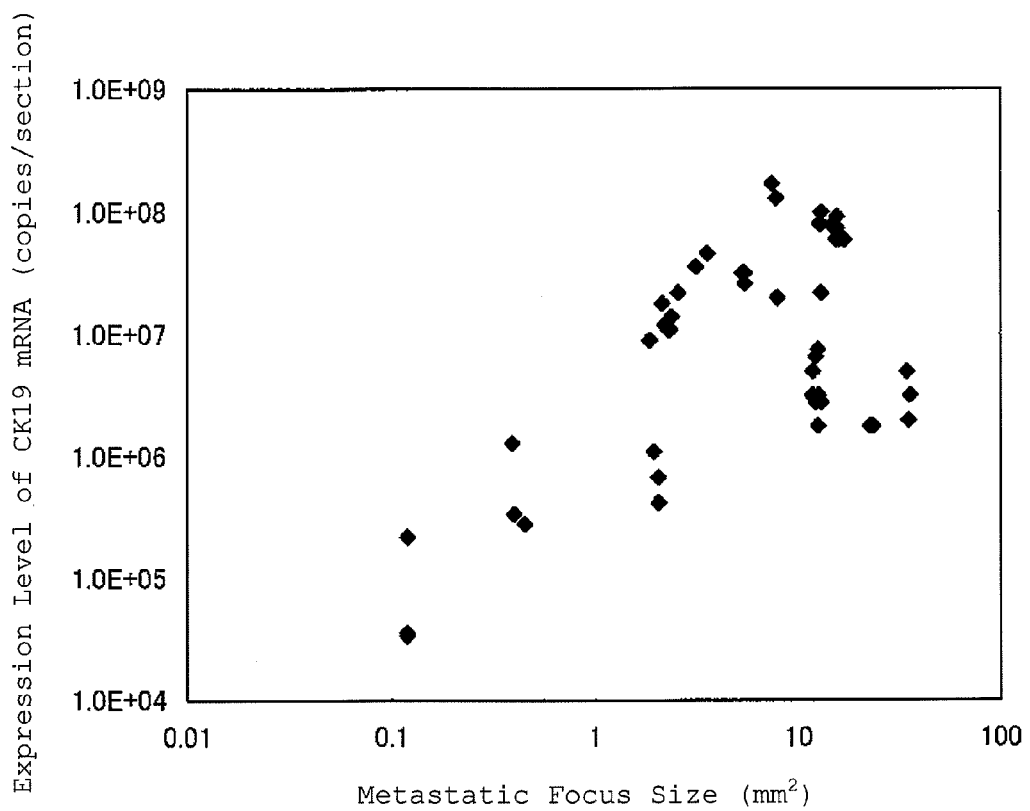
FIG. 10 is a graph showing the relationship between a quantitative value of mRNA of CK19 and the size of a metastatic focus.
Figure 11:
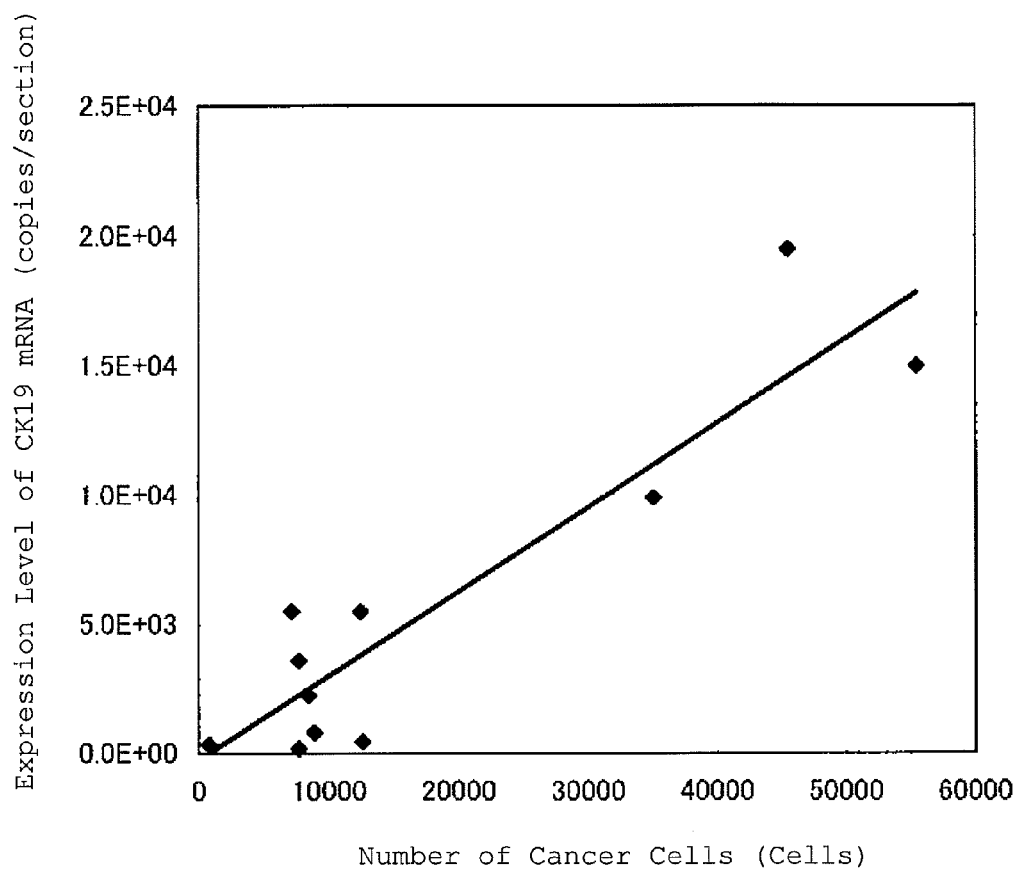
FIG. 11 is a graph showing the relationship between a quantitative value of mRNA of CK19 and the number of cancer cells.

The relationship between the quantitative value of mRNA (copies/section) and the size of a stomach cancer metastatic focus is shown in FIG. 10. The relationship between the quantitative value and the number of cancer cells is shown in FIG. 11. From FIGS. 10 and 11, it was recognized that the quantitative value of CK19 mRNA is correlated with the size of a metastatic focus and the number of cancer cells. Accordingly, it was confirmed that the size of the metastatic focus can be estimated by quantifying the CK19 mRNA in the lymph node.

What is claimed is:

1. A method of judging the lymph node metastasis of stomach cancer, comprising steps of:
   quantifying mRNA of cytokeratin 19 in a detection sample prepared from a lymph node tissue suspected of having stomach cancer metastasis, and
   judging the presence of lymph node metastasis of stomach cancer, on the basis of the obtained quantitative value of the mRNA
   wherein the quantifying step is performed by quantifying the mRNA of cytokeratin 19 by a nucleic acid amplification method selected from the group consisting of (i) quantitative RT-PCR using at least one primer selected from the group consisting of a primer having a nucleotide sequence set forth in SEQ NO 1 and a primer having a nucleotide sequence set forth in SEQ NO 2, and (ii) quantitative RT-LAMP using at least one primer selected from the group consisting of a primer having a nucleotide sequence set forth in SEQ NO 5 and a primer having a nucleotide sequence set forth in SEQ NO 6, and
   wherein the judging step is performed by comparing the quantitative value of the mRNA with a predetermined first and second threshold values, and
   determining the lymph node metastasis is negative when the quantitative value is lower than the first threshold value, the lymph node metastasis is micrometastasis when the quantitative value is equal to, or higher than, the first threshold value and simultaneously lower than the second threshold value, or the lymph node metastasis is macrometastasis when the quantitative value is equal to, or higher than, the second threshold.

2. The method of claim 1, wherein the quantitative value of the mRNA is the absolute amount of the mRNA of cytokeratin 19 in the detection sample.

3. A method of judging the lymph node metastasis of stomach cancer, comprising the steps of:
   quantifying mRNA of cytokeratin 19 in a detection sample prepared from a lymph node tissue suspected of having stomach cancer metastasis, and
   judging the presence of lymph node metastasis of stomach cancer, on the basis of the obtained quantitative value of the mRNA
   wherein the quantifying step is performed by quantifying the mRNA of cytokeratin 19 by quantitative RT-LAMP using at least two primers which are a primer having a nucleotide sequence set forth in SEQ NO 5 and a primer having a nucleotide sequence set forth in SEQ NO 6, and
   wherein the judging step is performed by comparing the quantitative value of the mRNA with a predetermined first and second threshold values, and
   determining the lymph node metastasis is negative when the quantitative value is lower than the first threshold value, the lymph node metastasis is micrometastasis when the quantitative value is equal to, or higher than, the first threshold value and simultaneously lower than the second threshold value, or the lymph node metastasis is macrometastasis when the quantitative value is equal to, or higher than, the second threshold.

4. The method of claim 3, wherein the quantitative RT-LAMP is performed by using at least one primer selected from the group consisting of a primer having a nucleotide sequence set forth in SEQ NO 7 and a primer having a nucleotide sequence set forth in SEQ NO 8, in addition to the primers in claim 3.

5. The method of claim 3, wherein the quantitative RT-LAMP is performed by using at least one primer selected from the group consisting of a primer having a nucleotide sequence set forth in SEQ NO 9 and a primer having a nucleotide sequence set forth in SEQ NO 10, in addition to the primer in claim 3.

6. A method of judging the lymph node metastasis of stomach cancer, comprising steps of:
   quantifying mRNA of cytokeratin 19 in a detection sample prepared from a lymph node tissue suspected of having stomach cancer metastasis, and
   judging the presence or absence of lymph node metastasis of stomach cancer, on the basis of the obtained quantitative value of the mRNA
   wherein the quantifying step is performed by performing the mRNA of cytokeratin 19 by a nucleic acid amplification method selected from the group consisting of (i) quantitative RT-PCR using at least one primer selected from the group considering of a primer having a nucleotide set forth in SEQ NO 1 and a primer having a nucleotide sequence set forth in SEQ NO 2, and (ii) quantitative RT-LAMP using at least one primer selected from the group consisting of a primer having a nucleotide sequence set forth in SEQ NO 5 and a primer having a nucleotide sequence set forth in SEQ NO 6, and
wherein the judging step is performed by comparing the quantitative value of the mRNA with a predetermined first and second threshold values,
determining the lymph node metastasis is negative when the quantitative value is lower than the first threshold value, the lymph node metastasis is micrometastasis when the quantitative value is equal to, or higher than, the first threshold value and simultaneously lower than the second threshold value, or the lymph node metastasis is macrometastasis when the quantitative value is equal to, or higher than, the second threshold, and
wherein the quantitative value is not standardized.

* * * * *